United States Patent
O'Brien

(10) Patent No.: US 7,538,187 B2
(45) Date of Patent: May 26, 2009

(54) COLORING COMPOSITIONS WITH PEPTIDE-BASED DISPERSANTS AND BINDERS

(75) Inventor: John P. O'Brien, Oxford, PA (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 162 days.

(21) Appl. No.: 11/194,834

(22) Filed: Aug. 1, 2005

(65) Prior Publication Data

US 2007/0022547 A1 Feb. 1, 2007

(51) Int. Cl.
*C07K 14/00* (2006.01)
*D06P 1/00* (2006.01)
*C07K 7/00* (2006.01)

(52) U.S. Cl. .............................. 530/324; 514/2; 8/445; 8/636; 8/637.1

(58) Field of Classification Search .................... 514/2; 8/445, 636, 637.1; 530/324
See application file for complete search history.

(56) References Cited

U.S. PATENT DOCUMENTS

| 5,085,698 | A | 2/1992 | Ma et al. |
| 5,124,438 | A | 6/1992 | Brueckmann et al. |
| 6,306,993 | B1 * | 10/2001 | Rothbard et al. ............ 526/304 |
| 6,689,870 | B1 * | 2/2004 | Yang et al. .................. 530/402 |
| 7,214,766 | B2 * | 5/2007 | Everett et al. ............... 530/300 |
| 2005/0054752 | A1 | 3/2005 | O'Brien et al. |

FOREIGN PATENT DOCUMENTS

| EP | 1 275 728 A1 | 1/2003 |
| WO | WO 98/00500 A1 | 1/1998 |
| WO | WO 00/18897 A1 | 4/2000 |
| WO | WO 01/32848 A1 | 5/2001 |

OTHER PUBLICATIONS

English Abstract of Han [Acta Biochimica et Biophysica Sinica 30(3), 263-266, 1998].*
U.S. Appl. No. 10/935,254, filed Sep. 7, 2004, John P. O'Brien et al.

* cited by examiner

*Primary Examiner*—David Lukton

(57) ABSTRACT

Coloring compositions comprising peptide-based dispersants and/or binders are provided. The compositions are particularly useful for the coloring or dyeing of substrates such as paper and textile fabrics. The peptide-based dispersant and/or binder compositions are distinguished by the presence of at least one positively charged terminal amino acid on the peptide portion of the composition which enhances binding to the substrate.

27 Claims, No Drawings

SEQUENCE LISTING

<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Peptide-based dispersant and binder

<400> SEQUENCE: 1

Lys Met Pro Pro Pro Leu Met Gln
1               5

<210> SEQ ID NO 2
<211> LENGTH: 8
<212> TYPE: PRT

```
<213> ORGANISM: Artificial Sequence
<220> FEATURE:
<223> OTHER INFORMATION: Peptide-based dispersant and binder

<400> SEQUENCE: 2

Lys Tyr Pro Asn Thr Ala Leu Val
1               5

<210> SEQ ID NO 3
<211> LENGTH: 12
<212> TYPE: PRT
<213> ORGANISM: Artificial Sequence
<220> FEATURE:
<223> OTHER INFORMATION: Affinity peptide having binding affinity for
      carbon black pigment

<400> SEQUENCE: 3

Arg Thr Ala Pro Thr Thr Pro Leu Leu Leu Ser Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Affinity peptide having binding affinity for
      cellulose

<400> SEQUENCE: 4

Thr His Lys Thr Ser Thr Gln Arg Leu Leu Ala Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Affinity peptide having binding affinity for
      cotton

<400> SEQUENCE: 5

Ser Ile Leu Pro Tyr Pro Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Affinity peptide having binding affinity for
      carbon black pigment

<400> SEQUENCE: 6

Phe His Glu Asn Trp Pro Ser
1               5

<210> SEQ ID NO 7
<211> LENGTH: 12
<212> TYPE: PRT
<213> ORGANISM: Artificial Sequence
<220> FEATURE:
<223> OTHER INFORMATION: Peptide-based binder

<400> SEQUENCE: 7

Lys Pro Pro Pro Pro Ser Thr Ala Ser Tyr Thr Arg
1               5                   10
```

```
<210> SEQ ID NO 8
<211> LENGTH: 20
<212> TYPE: PRT
<213> ORGANISM: Artificial Sequence
<220> FEATURE:
<223> OTHER INFORMATION: Peptide-based dispersant and binder
<220> FEATURE:
<221> NAME/KEY: MISC_FEATURE
<222> LOCATION: (1)..(8)
<223> OTHER INFORMATION: The lysine residues at posiitons 1-8 are
      optionally present or absent

<400> SEQUENCE: 8

Lys Lys Lys Lys Lys Lys Lys Lys Lys Lys Lys Lys Met Pro Pro
1               5                   10                  15

Pro Leu Met Gln
            20

<210> SEQ ID NO 9
<211> LENGTH: 18
<212> TYPE: PRT
<213> ORGANISM: Artificial Sequence
<220> FEATURE:
<223> OTHER INFORMATION: Peptide-based dispersant and binder
<220> FEATURE:
<221> NAME/KEY: MISC_FEATURE
<222> LOCATION: (1)..(9)
<223> OTHER INFORMATION: The lysine residues at positions 1-9 are
      optionally present or absent

<400> SEQUENCE: 9

Lys Lys Lys Lys Lys Lys Lys Lys Lys Lys Tyr Pro Asn Thr Ala
1               5                   10                  15

Leu Val

<210> SEQ ID NO 10
<211> LENGTH: 32
<212> TYPE: PRT
<213> ORGANISM: Artificial Sequence
<220> FEATURE:
<223> OTHER INFORMATION: Peptide-based dispersant and binder
<220> FEATURE:
<221> NAME/KEY: MISC_FEATURE
<222> LOCATION: (1)..(15)
<223> OTHER INFORMATION: The lysine residues at positions 1-15 are
      optionally present or absent

<400> SEQUENCE: 10

Lys Lys Lys Lys Lys Lys Lys Lys Lys Lys Lys Lys Lys Lys Lys
1               5                   10                  15

Lys Lys Lys Lys Arg Thr Ala Pro Thr Thr Pro Leu Leu Leu Ser Leu
            20                  25                  30

<210> SEQ ID NO 11
<211> LENGTH: 42
<212> TYPE: PRT
<213> ORGANISM: Artificial Sequence
<220> FEATURE:
<223> OTHER INFORMATION: Peptide-based binder
<220> FEATURE:
<221> NAME/KEY: MISC_FEATURE
<222> LOCATION: (1)..(26)
<223> OTHER INFORMATION: The lysine residues at positions 1-26 are
      optionally present or absent

<400> SEQUENCE: 11

Lys Lys Lys Lys Lys Lys Lys Lys Lys Lys Lys Lys Lys Lys Lys
1               5                   10                  15
```

```
Lys Lys Lys Lys Lys Lys Lys Lys Lys Lys Lys Lys Thr His
            20                  25                  30

Lys Thr Ser Thr Gln Arg Leu Leu Ala Ala
            35                  40

<210> SEQ ID NO 12
<211> LENGTH: 27
<212> TYPE: PRT
<213> ORGANISM: Artificial Sequence
<220> FEATURE:
<223> OTHER INFORMATION: Peptide-based binder
<220> FEATURE:
<221> NAME/KEY: MISC_FEATURE
<222> LOCATION: (1)..(19)
<223> OTHER INFORMATION: The lysine residues at positions 1-19 are
      optionally present or absent

<400> SEQUENCE: 12

Lys Lys Lys Lys Lys Lys Lys Lys Lys Lys Lys Lys Lys Lys Lys Lys
1               5                   10                  15

Lys Lys Lys Lys Ser Ile Leu Pro Tyr Pro Tyr
            20                  25

<210> SEQ ID NO 13
<211> LENGTH: 32
<212> TYPE: PRT
<213> ORGANISM: Artificial Sequence
<220> FEATURE:
<223> OTHER INFORMATION: Peptide-based dispersant and binder
<220> FEATURE:
<221> NAME/KEY: MISC_FEATURE
<222> LOCATION: (1)..(22)
<223> OTHER INFORMATION: The lysine residues at positions 1-22 are
      optionally present or absent

<400> SEQUENCE: 13

Lys Lys Lys Lys Lys Lys Lys Lys Lys Lys Lys Lys Lys Lys Lys Lys
1               5                   10                  15

Lys Lys Lys Lys Lys Lys Lys Lys Phe His Glu Asn Trp Pro Ser
            20                  25                  30

<210> SEQ ID NO 14
<211> LENGTH: 47
<212> TYPE: PRT
<213> ORGANISM: Artificial Sequence
<220> FEATURE:
<223> OTHER INFORMATION: Peptide-based binder
<220> FEATURE:
<221> NAME/KEY: MISC_FEATURE
<222> LOCATION: (20)..(47)
<223> OTHER INFORMATION: The lysine residues at positions 20-47 are
      optionall present or absent

<400> SEQUENCE: 14

Lys Pro Pro Pro Pro Ser Thr Ala Ser Tyr Thr Arg Lys Lys Lys Lys
1               5                   10                  15

Lys Lys Lys Lys Lys Lys Lys Lys Lys Lys Lys Lys Lys Lys Lys Lys
            20                  25                  30

Lys Lys Lys Lys Lys Lys Lys Lys Lys Lys Lys Lys Lys Lys Lys
            35                  40                  45

<210> SEQ ID NO 15
<211> LENGTH: 14
<212> TYPE: PRT
<213> ORGANISM: Artificial Sequence
<220> FEATURE:
<223> OTHER INFORMATION: Peptide-based dispersant and binder
```

```
<400> SEQUENCE: 15

Phe His Glu Asn Trp Pro Ser Pro Pro Lys Lys Lys Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Peptide-based dispersant and binder

<400> SEQUENCE: 16

Phe His Glu Asn Trp Pro Ser Pro Pro Arg Arg Arg Arg
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Peptide-based dispersant and binder

<400> SEQUENCE: 17

Phe His Glu Asn Trp Pro Ser Lys
1               5

<210> SEQ ID NO 18
<211> LENGTH: 12
<212> TYPE: PRT
<213> ORGANISM: Artificial Sequence
<220> FEATURE:
<223> OTHER INFORMATION: Peptide-based binder

<400> SEQUENCE: 18

Lys Pro Pro Pro Pro Ser Ile Leu Pro Tyr Pro Tyr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Peptide-based binder

<400> SEQUENCE: 19

Lys Pro Pro Pro Pro Ser Thr Ala Ser Tyr Thr Arg
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Peptide-based binder

<400> SEQUENCE: 20

Lys Ser Ile Leu Pro Tyr Pro Tyr Pro Pro Ser Thr Ala Ser Tyr
1               5                   10                  15

Thr Arg

<210> SEQ ID NO 21
<211> LENGTH: 18
<212> TYPE: PRT
<213> ORGANISM: Artificial Sequence
<220> FEATURE:
```

```
<223> OTHER INFORMATION: Peptide-based binder

<400> SEQUENCE: 21

Lys Ser Ile Leu Pro Tyr Pro Tyr Pro Pro Ser Ile Leu Pro Tyr
1               5                   10                  15

Pro Tyr

<210> SEQ ID NO 22
<211> LENGTH: 7
<212> TYPE: PRT
<213> ORGANISM: Artificial Sequence
<220> FEATURE:
<223> OTHER INFORMATION: Affinity peptide having binding affinity for
      cellulose

<400> SEQUENCE: 22

Val Pro Arg Val Thr Ser Ile
1               5

<210> SEQ ID NO 23
<211> LENGTH: 7
<212> TYPE: PRT
<213> ORGANISM: Artificial Sequence
<220> FEATURE:
<223> OTHER INFORMATION: Affinity peptide having binding affinity for
      carbon black pigment

<400> SEQUENCE: 23

Met Pro Pro Pro Leu Met Gln
1               5

<210> SEQ ID NO 24
<211> LENGTH: 7
<212> TYPE: PRT
<213> ORGANISM: Artificial Sequence
<220> FEATURE:
<223> OTHER INFORMATION: Affinity peptide having binding affinity for
      Sunfast Magenta pigment

<400> SEQUENCE: 24

Tyr Pro Asn Thr Ala Leu Val
1               5

<210> SEQ ID NO 25
<211> LENGTH: 12
<212> TYPE: PRT
<213> ORGANISM: Artificial Sequence
<220> FEATURE:
<223> OTHER INFORMATION: Affinity peptide having binding affinity for
      carbon black pigment

<400> SEQUENCE: 25

Trp His Leu Ser Trp Ser Pro Val Pro Leu Pro Thr
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Affinity peptide having binding affinity for
      cotton

<400> SEQUENCE: 26

Ser Thr Ala Ser Tyr Thr Arg
1               5
```

COLORING COMPOSITIONS WITH PEPTIDE-BASED DISPERSANTS AND BINDERS

FIELD OF THE INVENTION

The invention relates to peptide-based compositions that can function as pigment dispersants and/or binders. Specifically, a composition is provided comprising a peptide adhered to a pigment, the peptide having at least one positively charged terminal amino acid and at least one block segment that has affinity for pigment or substrate surfaces.

BACKGROUND OF THE INVENTION

The digital printing of textiles is a large and growing business market. To meet the needs of this market, pigment dispersants and binders that disperse and durably bind pigments to a variety of fabric surfaces are required. Polymeric dispersants are widely used to stabilize pigments in ink jet printing inks. The dispersant serves to form a shell around the pigment particle, preventing flocculation and coagulation. Additionally, polymer-based binders may be added to the ink composition to enhance the binding of the pigment to the fabric surface.

Proteins and peptides have also been used as dispersants and film-forming binders in coloring compositions. For example, Brueckmann et al. in U.S. Pat. No. 5,124,438 describe the use of chemically modified proteins, such as casein, collagen, albumin and gelatin, as dispersants in color formulations. Additionally, cellulose binding domains (CBDs) from various enzymes, such as cellulases, xylanases, mannanases, arabinofuranosidases, acetyl esterases, and chitinases, have been used in compositions for treating cellulosic fabrics to ensure the deposition of a benefit agent onto the fabric (Jones et al. in WO 9800500 and Smets et al. in WO 01/18897). Mimic CBDs, which are synthetic peptides of 30 or fewer amino acids, preferably containing at least three aromatic amino acids, have also been used to link various benefit agents to cellulosic fabrics (Bjorkquist et al., WO 0132848).

Han et al. (*Shengwu Huaxue Yu Shengwu Wuli Xuebao* 30:263-266 (1998)) describe the identification of peptides that specifically bind to a cellulose matrix using phage display screening. The deduced amino acid sequences of these cellulose-binding peptides have a conserved aromatic residue, tyrosine or phenylalanine, which is similar to the normal cellulose-binding domain of cellulose-binding proteins. The use of these cellulose-binding peptides in new dispersants and/or binders for coloring applications is not described in that disclosure.

Nomoto et al in EP1275728 describe the identification of pigment-binding peptides using phage display. Some carbon black, copper phthalocyanine, titanium dioxide, and silicon dioxide-binding peptide sequences are disclosed. However, the use of the pigment-binding peptides as dispersants and/or binders for coloring applications is not described.

O'Brien et al. in copending and commonly owned U.S. patent application Ser. No. 10/935,254 and U.S. Application Publication No. 20050054752 describe peptides, identified by phage display screening, that bind with high affinity to pigments and print media. The peptides were used to prepare diblock and triblock dispersants and/or binders that provide improved durability for coloring applications. However, improved dispersants and/or binders that provide greater durability, particularly for textile fabric printing, are still required.

Therefore, the problem to be solved is to provide pigment dispersant and/or binders that effectively disperse pigments and provide improved durability to meet the demanding-needs of more advanced, high quality coloring applications, such as textile printing.

Applicants have addressed the stated problem by discovering that the addition of at least one positively charged amino acid residue at the N-terminal and/or C-terminal end of the sequence of a peptide having binding affinity for pigment or substrate surfaces significantly enhances the strength of the interaction of the peptide with substrate surfaces. These affinity peptides having at least one terminal positively charged amino acid residue function as pigment dispersants and/or binders that provide significantly improved durability on textile fabrics compared to conventional polymeric dispersants and binders or the unmodified affinity peptides.

SUMMARY OF THE INVENTION

The invention relates to the peptides that facilitate the binding of pigments to substrates used in the printing industry. Provided herein are peptides having at least one positively charged amino acid residue at the N-terminal and/or C-terminal end of the sequence that, when added to a composition comprising a pigment, server to enhance the binding of the pigment to the substrate. Accordingly the invention provides a coloring composition for coloring a substrate comprising:
  a) a pigment;
  b) a carrier medium; and
  c) a peptide having affinity for a substrate and having the general formula:

$(nA^+)_x\text{-(Sn)-AP-(Sc)-}(cA^+)_y$ wherein:
    (i) $nA^+$ is a positively charged amino acid at the N-terminal end of the peptide, selected from the group consisting of lysine and arginine;
    (ii) $cA^+$ is a positively charged amino acid at the C-terminal end of the peptide, selected from the group consisting of lysine and arginine;
    (iii) AP is an affinity peptide having an amino acid sequence that has a binding affinity for the pigment;
    (iv) x=0 to about 50;
    (v) y=0 to about 50; and
    (vi) Sn and Sc are optional spacers comprised of 0 to about 20 amino acids;
    provided that x and n may not both be 0.

In an alternate embodiment the invention provides a coloring composition for coloring a substrate comprising:
  a) a dispersed pigment;
  b) a carrier medium; and
  c) a peptide having affinity for a substrate and having the general formula:

$(nA^+)_x\text{-(Sn)-AP-(Sc)-}(cA^+)_y$ wherein:
    (i) $nA^+$ is a positively charged amino acid at the N-terminal end of the peptide, selected from the group consisting of lysine and arginine;
    (ii) $cA^+$ is a positively charged amino acid at the C-terminal end of the peptide, selected from the group consisting of lysine and arginine;
    (iii) AP is an affinity peptide having an amino acid sequence that has a binding affinity for the pigment or the substrate;
    (iv) x=0 to about 50;
    (v) y=0 to about 50; and (vi) Sn and Sc are optional spacers comprised of 0 to about 20 amino acids;

provided that x and y may not both be 0.

In another embodiment the invention provides an ink comprising the coloring composition of the invention.

In an alternate embodiment the invention provides a method for dyeing a substrate comprising applying the coloring composition of the invention under conditions whereby the substrate is dyed.

In another embodiment the invention provides peptides having the amino acid sequence selected from the group consisting of SEQ ID NOs:1, 2, 7, 8, 9, 10, 11, 12, 13, 14, 15, 16, 17, 18, 19, 20, and 21.

In another embodiment the invention provides peptide having affinity for a substrate having the general formula:

$(nA^+)_x$-(Sn)-AP-(Sc)-$(cA^+)_y$ wherein:

(i) $nA^+$ is a positively charged amino acid at the N-terminal end of the peptide, selected from the group consisting of lysine and arginine;

(ii) $cA^+$ is a positively charged amino acid at the C-terminal end of the peptide, selected from the group consisting of lysine and arginine;

(iii) AP is an affinity peptide having an amino acid sequence that has a binding affinity for the pigment or the substrate;

(iv) x=0 to about 50;

(v) y=0 to about 50; and (vi) Sn and Sc are optional spacers comprised of 0 to about 20 amino acids;

provided that x and n may not both be 0.

BRIEF DESCRIPTION OF THE SEQUENCE DESCRIPTIONS

The invention can be more fully understood from the following detailed description, and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs:1, 2, 8, 9, 10, 13, 15, 16, and 17 are the amino acid sequences of peptide-based pigment dispersants and binders of the invention.

SEQ ID NOs:7, 11, 12, 14, 18, 19, 20, and 21 are the amino acid sequences of peptide-based binders of the invention.

SEQ ID NOs:3, 4, 5, 6, 22, 23, 24, 25, and 26 are the amino acid sequences of affinity peptides having a binding affinity for pigment or print media surfaces.

DETAILED DESCRIPTION OF THE INVENTION

The invention provides peptide-based pigment dispersants and/or binders, which are formed by adding at least one positively charged amino acid residue to the N-terminal and/or C-terminal end of the sequence of a peptide that has binding affinity for pigment or substrate surfaces. The peptide-based pigment dispersants and/or binders are useful in coloring compositions, particularly for textile printing applications. The coloring compositions of the invention provide enhanced durability when coated on textile fabrics and other substrates.

The following definitions are used herein and should be referred to for interpretation of the Claims and the specification.

The term "peptide" refers to two or more amino acids joined to each other by peptide bonds or modified peptide bonds. As used herein, the terms "peptide", "polypeptide", and "protein" are used interchangeably.

The term "pigment" refers to an insoluble, organic or inorganic colorant.

The term "substrate" refers to any material or substance to be dyed or colored. Examples of substrates include, but are not limited to, printing paper, sheets, films, nonwovens and textile fabrics, such as polyester, nylon, Lycra®, silk, cotton, cotton blends, rayon, flax, linen, wool, spandex, acetate, acrylic, modacrylic, aramid and polyolefin.

The term "dispersant" as used herein refers to a substance that stabilizes the formation of a colloidal solution of solid pigment particles in a liquid medium.

The term "binder" as used herein refers to a substance that provides an enhanced interaction between the pigment and the surface of a substrate.

The terms "affinity peptide" and "binding peptide" are used interchangeably herein to refer to amino acid sequences that have a specific binding affinity for pigment or substrate surfaces.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

Standard recombinant DNA and molecular cloning techniques used herein are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Spring Harbor, N.Y. (1984); and by Ausubel, F. M. et al., *Current Protocols in Molecular Biology*, published by Greene Publishing Assoc. and Wiley-Interscience (1987).

The invention provides peptide-based pigment dispersants and/or binders, which are formed by adding at least one positively charged amino acid residue to the N-terminal and/or the C-terminal end of the sequence of a peptide that has binding affinity for pigment or substrate surfaces. The affinity peptides are identified by combinatorial methods such as phage display screening. The affinity peptides with at least one terminal positively charged amino acid residue function as pigment dispersants and/or binders that provide significantly improved durability on textile fabrics compared to conventional polymeric dispersants and binders or the unmodified affinity peptides.

Pigments

As used herein, the term "pigment" means an insoluble colorant. A wide variety of organic and inorganic pigments alone or in combination may be used in the present invention. Representative examples of organic pigments include, but are not limited to, (cyan) Pigment Blue 15:3 and Pigment Blue 15:4; (magenta) Pigment Red 122 and Pigment Red 202; (yellow) Pigment Yellow 14, Pigment Yellow 74, Pigment Yellow 95, Pigment Yellow 110, Pigment Yellow 114, Pigment Yellow 128 and Pigment Yellow 155; (red) Pigment Orange 5, Pigment Orange 34, Pigment Orange 43, Pigment Orange 62, Pigment Red 17, Pigment Red 49:2, Pigment Red 112, Pigment Red 149, Pigment Red 177, Pigment Red 178, Pigment Red 188, Pigment Red 255 and Pigment Red 264; (green) Pigment Green 1, Pigment Green 2, Pigment Green 7 and Pigment Green 36; (blue) Pigment Blue 60, Pigment Violet 3, Pigment Violet 19, Pigment Violet 23, Pigment Violet 32, Pigment Violet 36 and Pigment Violet 38; and (black) carbon black. Preferred organic pigments are carbon black, Pigment Blue 15:3, Pigment Blue 15:4, Pigment Red 122, Pigment Red 202, Pigment Yellow 14, Pigment Yellow 74, Pigment Yellow 95, Pigment Yellow 110, Pigment Yellow 128 and Pigment Yellow 155. Colorants are referred to herein by their "C.I." designation established by Society Dyers and Colourists, Bradford, Yorkshire, UK and published in the *The Color Index*, Third Edition, 1971. Examples of inorganic pigments include, but are not limited to finely divided metals, such as copper, iron, aluminum, and alloys thereof; and metal oxides, such as silica, alumina, and titania.

Substrates

The term "substrate" as used herein refers to any material or substance to be dyed or colored. Preferred substrates are print media that are suitable for ink jet printing. Suitable print media include, but are not limited to, printing paper, sheets, films, nonwovens and textile fabrics, such as polyester, nylon, Lycra®, silk, cotton, cotton blends, rayon, flax, linen, wool, spandex, acetate, acrylic, modacrylic, aramid and polyolefin. These substrates are readily available from a number of commercial sources.

Pigment-Binding and Substrate-Binding Affinity Peptides

Pigment-binding peptides and substrate-binding peptides as defined herein are peptide sequences that specifically bind with high affinity to pigments and substrates, respectively. The pigment-binding peptides and the substrate-binding peptides of the present invention are from about 4 amino acids to 20 amino acids, more preferably, from about 4 amino acids to about 12 amino acids in length.

Suitable pigment-binding peptide and substrate-binding peptide sequences may be selected using methods that are well known in the art, such as described by O'Brien et al in U.S. Application Publication No. 20050054752, which is incorporated herein by reference. The peptides of the present invention are generated randomly and then selected against a specific pigment or a specific substrate based upon their binding affinity for the pigment or substrate of interest. The generation of random libraries of peptides is well known and may be accomplished by a variety of techniques including, bacterial display (Kemp, D. J.; *Proc. Natl. Acad. Sci. USA* 78(7): 4520-4524 (1981), and Helfman et al., *Proc. Natl. Acad. Sci. USA* 80(1):31-35, (1983)), yeast display (Chien et al., *Proc Natl Acad. Sci USA* 88(21):9578-82 (1991)), combinatorial solid phase peptide synthesis (U.S. Pat. Nos. 5,449,754, 5,480,971, 5,585,275, 5,639,603), and phage display technology (U.S. Pat. Nos. 5,223,409, 5,403,484, 5,571,698, 5,837, 500). Techniques to generate such biological peptide libraries are well known in the art. Exemplary methods are described in Dani, M., *J. of Receptor & Signal Transduction Res.*, 21 (4):447-468 (2001), Sidhu et al., *Methods in Enzymology* 328:333-363 (2000), and *Phage Display of Peptides and Proteins, A Laboratory Manual*, Brian K. Kay, Jill Winter, and John McCafferty, eds.; Academic Press, NY, 1996. Additionally, phage display libraries are available commercially from companies such as New England BioLabs (Beverly, Mass.).

A preferred method to randomly generate peptides is by phage display. Phage display is an in vitro selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". In its simplest form, biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

The affinity peptides of the invention may be selected using the following procedure. After a suitable library of phage peptides has been generated, they are then contacted with an appropriate amount of a selected pigment or a specific substrate. The pigment or substrate is presented to the library of phage peptides while suspended in solution or immobilized on a plate or bead. A preferred solution is a buffered aqueous saline solution containing a surfactant. A suitable solution is Tris-buffered saline (TBS) with 0.1% Tween® 20. The solution may additionally be agitated by any means in order to increase the mass transfer rate of the phage peptides to the pigment or substrate surface, thereby shortening the time required to attain maximum binding. Upon contact, a number of the randomly generated phage peptides will bind to the pigment or substrate to form a phage peptide-pigment or a peptide-substrate complex. Unbound phage peptide may be removed by washing. After all unbound material is removed, phage peptides having varying degrees of binding affinities for the pigment or substrate may be fractionated by selected washings in buffers having varying stringencies. Increasing the stringency of the buffer used increases the required strength of the bond between the phage peptide and the pigment in the phage peptide-pigment complex or between the phage peptide and the substrate in the phage peptide-substrate complex.

A number of substances may be used to vary the stringency of the buffer solution in phage peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P40, Triton X-100, Tween® 20, wherein Tween®) 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that phage peptides having increasing binding affinities for the pigment or substrate may be eluted by repeating the selection process using buffers with increasing stringencies. The eluted phage peptides may be identified and sequenced using any means known in the art.

Useful affinity peptide sequences include, but are not limited to, peptides having a binding affinity for the pigments carbon black, Cromophthal® Yellow, Sunfast® Magenta, and Sunfast® Blue, and peptides having a binding affinity for the print media cellulose, polyester, cotton, polyester/cotton, and printing paper, as described by O'Brien et al, supra. Exemplary affinity peptide sequences that have affinity for pigment or print media surfaces are given as SEQ ID NOs:3, 6, 23, 24, and 25, and SEQ ID NOs:4, 5, 22, and 26, respectively. Additionally, the affinity peptide may be a diblock or triblock composition comprising two print media binding peptide sequences or a pigment binding peptide sequence and a print medium binding sequence, as disclosed by O'Brien et al., supra. In the triblock compositions, the two binding peptide blocks are connected through a spacer as disclosed by O'Brien et al., supra.

Production of Affinity Peptides

The affinity peptides may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding the pigment or substrate-binding peptides may be produced in heterologous host cells, particularly in the cells of microbial hosts, as described by O'Brien et al., supra.

Peptide-Based Dispersants and/or Binders

The peptide-based dispersants and/or binders of the invention are peptides that are prepared by adding at least one positively charged amino acid residue at the N-terminal and/or the C-terminal end of the sequence of an affinity peptide. The peptide-based dispersants and binders of the invention comprise an affinity peptide that has a binding affinity for a pigment, and therefore can serve as both a dispersant and a binder. The peptide-based binders of the invention comprise an affinity peptide that has a binding affinity for a substrate. Preferably, more than one positively charged amino acid residue is added to either or both of the N-terminal or C-terminal end of the sequence of the affinity peptide. The number of positively charged amino acid residues added to at least one terminal end of the affinity peptide ranges from 1 to about 50. Preferably, the positively charged amino acid is lysine or arginine. If more than one positively charged amino acid is added, a combination of the aforementioned positively charged amino acids may be used.

Optionally, the positively charged amino acids may be added to the C-terminal or N-terminal end or to both ends of the affinity peptide sequence by attachment via a spacer. The spacer may be comprised of any combination of amino acids that provide the required spacing and meet the solubility requirements for the particular coloring formulation. Preferably, the spacer is comprised of the amino acids proline, glycine, alanine, serine, glutamic acid, aspartic acid, lysine, histidine, arginine, and mixtures thereof. To increase the water solubility of the peptide-based dispersant and/or binder, a spacer comprised of polar amino acids, including but not limited to, serine, glutamic acid, aspartic acid, lysine, histidine, arginine, and mixtures thereof may be used. The amino acid spacer may be from 1 to about 20 amino acids in length.

In one embodiment, the peptide-based dispersants and/or binders of the invention are peptides that may be represented by the following general formula:

wherein: $nA^+$ is a positively charged amino acid at the N-terminal end of the peptide; $cA^+$ is a positively charged amino acid at the C-terminal end of the peptide; the positively charged amino acid is lysine or arginine, Sn and Sc are optional spacers comprised of 0 to about 20 amino acids; AP is an affinity peptide having an amino acid sequence that has a binding affinity for the pigment or a substrate; x=0 to about 50; y=0 to about 50, provided that x and y may not both be 0. Exemplary affinity peptides are given by SEQ ID NOs:3, 4, 5, 6, 22, 23, 24, 25, and 26. Preferably, the peptide-based dispersant and/or binder is from about 5 amino acids to about 100 amino acids, more preferably from about 5 amino acids to about 30 amino acids, most preferably from about 5 amino acids to about 20 amino acids in length. Exemplary peptide sequences for the peptide-based dispersants and binders of the invention are given by SEQ ID NOs:1, 2, 8, 9, 10, 13, 15, 16, and 17. The peptide-based binders of the invention are exemplified by SEQ ID NOs:7, 11, 12, 14, 18, 19, 20, and 21.

The peptide-based dispersants and/or binders of the invention may be prepared by adding the positively charged amino acid residue(s) at either or both ends of the affinity peptide sequence using standard peptide synthesis methods or using recombinant DNA and molecular cloning techniques, as described above. Alternatively, the positively charged amino acid may be added to the affinity peptide sequence by the in situ polymerization of the N-carboxyanhydride of the desired amino acid(s) via activation through the N-terminal amine of the pigment-binding peptide. This approach is based on the known ability of primary amines to catalyze the ring opening polymerization of N-carboxyanhydrides (see for example, Penczek, *Models of Ring Opening Polymerization*, CRC Press, Boca Raton, Fla. (1989)). In addition, the peptide blocks may be prepared separately using the methods described above and combined using carbodiimide coupling agents (see for example, Hermanson, *Bioconjugate Techniques*, Academic Press, New York (1996)), diacid chlorides, diisocyanates and other bifunctional coupling reagents that are reactive to terminal amine and/or carboxylic acid terminal groups on the peptides.

The peptide-based dispersants and/or binders of the invention have a stronger affinity for substrate surfaces compared to the affinity peptides alone. Additionally, due to their interaction with pigments, the peptide-based dispersants and/or binders provide more secure attachment of pigments to substrate surfaces, resulting in more durable color coatings. The binding energy, herein defined as the amount of energy released upon the interaction of the peptide-based dispersants and/or binders of the invention with various substrates in units of kilocalories per mole (kcal/mol), provides an indication of the strength of the binding affinity. Therefore, the molar heat of adsorption for the interaction of the peptide-based dispersants and/or binders of the invention with substrate surfaces may be used as a measure of the binding energy of the interaction. The peptide-based dispersants and/or binders of the invention have an exothermic molar heat of adsorption when they bind to substrate surfaces from water of at least about 70 kcal/mol, as measured by flow microcalorimetry. The molar heats of adsorption may be measured using standard calorimetric measurement techniques using a flow microcalorimeter, such as that available from Microscal, London, Ltd, as described in detail in Examples 23-31. Briefly, the measurement of the molar heat of adsorption of the peptide-based dispersants and/or binders for the interaction with a substrate is accomplished by passing a solution containing a known concentration of the peptide-based dispersant and/or binder in water over a known amount of the substrate in the flow microcalorimeter and measuring the amount of heat released as a result of the binding interaction by means of thermistors contained in the microcalorimeter. The mass transfer value, defined herein as the amount of the binding peptide adsorbed per unit area of substrate, may be determined by means of a mass sensitive detector, such as a refractometer, located downstream of the flow microcalorimeter. The molar heat of adsorption may then be calculated by dividing the heat of adsorption obtained from the microcalorimetry determination by the mass transfer value. For an exothermic process, the molar heat of adsorption is given as a negative value to indicate that heat is released in the process. Additionally, the binding affinity may be measured using accelerated laundering tests, such as American Association of Textile Chemists and Colorists (AATCC) Method 61-1996, as described in Examples 8-22.

Coloring Compositions

The peptide-based dispersants and/or binders of the invention may be used in various coloring compositions to color, dye or print on various substrates. The coloring compositions of the invention have enhanced affinity for the substrate compared to conventional coloring compositions known in the art. Coloring compositions are well known in the art and typically comprise a dispersed pigment, and a carrier medium.

The carrier medium may be aqueous or nonaqueous, preferably the carrier medium is aqueous. The term "aqueous carrier medium" refers to a medium comprised of water or water and one or more organic, water-soluble components commonly referred to as co-solvents or humectants. Sometimes, when a co-solvent can assist in the penetration and drying of a colorant on a substrate, it is referred to as a penetrant. Representative examples of water-soluble organic solvents/humectants that may be used in the invention are disclosed in U.S. Pat. No. 5,085,698, which is incorporated herein by reference. Preferred water-soluble organic solvents include mono or polyhydric alcohols, glycol ethers or esters, glycols, and ketones. If a mixture of water and a water-soluble solvent is used, the aqueous carrier medium typically contains about 30% to about 95% water with the balance (i.e., about 70% to about 5%) being the water-soluble solvent.

"Nonaqueous carrier medium" refers to a medium that is substantially comprised of a nonaqueous solvent or mixtures of such solvents, which solvents can be polar and/or nonpolar. Examples of polar solvents include alcohols, esters, ketones, aliphatic organic acids, and ethers, particularly mono- and di-alkyl ethers of glycols and polyglycols such as monomethyl ethers of mono-, di- and tri-propylene glycols and the mono-n-butyl ethers of ethylene, diethylene and triethylene glycols. Preferred polar solvents include: dimethylformamide (DMF), dimethyl sulfoxide (DMSO), dimethyl acetamide (DMAC), N-methylpyrrolidone (NMP), tetrahydrofuran (THF), methanol, ethanol, propanol, isopropanol, butanol, isobutyl alcohol, tertiary butyl alcohol, ethylene glycol, trimethylene glycol, benzyl alcohol, formic acid, halogenated acetic acids such as trifluoroacetic acid, and mixtures thereof. Examples of nonpolar solvents include aliphatic and aromatic hydrocarbons having at least six carbon atoms and mixtures thereof including refinery distillation products and by-products. Even when no water is deliberately added to the nonaqueous carrier medium, some adventitious water may be carried into the formulation, but generally this will be no more than about 2-4%. By definition, the nonaqueous carrier medium of the invention will have no more than about 10%, and preferably no more than about 5%, by weight of water based on the total weight of the nonaqueous carrier medium.

The pigment may be a single pigment, or a mixture of pigments. Suitable pigments are given above. The coloring composition may contain from about 0.1% to about 50% by weight of the pigment relative to the total weight of the composition.

Pigments, by definition, are substantially insoluble in the carrier medium and therefore, are used in dispersed form. The pigment may be dispersed using a dispersant or a self-dispersing pigment may be used. When a dispersant is used to disperse the pigment, the dispersant may be any suitable dispersant known in the art, including, but not limited to, random or structured organic polymeric dispersants, as described below; protein dispersants, such as those described by Brueckmann et al. (U.S. Pat. No. 5,124,438); and peptide-based dispersants, such as those described by O'Brien et al, supra. Preferred random organic polymeric dispersants include acrylic polymer and styrene-acrylic polymers. Most preferred are structured dispersants, which include AB, BAB and ABC block copolymers, branched polymers and graft polymers. Preferably the organic polymers comprise monomer units selected from the group consisting of acrylate, methacrylate, butyl methacrylate, 2-ethylhexyl methacrylate, benzylmethacrylate, phenoxyethyl acrylate, and ethoxytriethyleneglycolmethacrylate, such as those described by Nigan (U.S. Patent Application Publication No. 2004/0232377). Some useful structured polymer dispersants are disclosed in U.S. Pat. No. 5,085,698, EP-A-0556649 and U.S. Pat. No. 5,231,131 (the disclosures of which are incorporated herein by reference).

A self-dispersing pigment is a pigment that has been surface modified with chemically attached, dispersibility imparting groups to allow stable dispersion without a separate dispersant. For dispersion in an aqueous carrier medium, surface modification involves addition of hydrophilic groups and most typically ionizable hydrophilic groups. The self-dispersing pigment may be prepared by grafting a functional group or a molecule containing a functional group onto the surface of the pigment, by physical treatment (such as vacuum plasma), or by chemical treatment (for example, oxidation with ozone, hypochlorous acid or the like). A single type or a plurality of types of hydrophilic functional groups may be bonded to one pigment particle. Self-dispersing pigments are described, for example, in U.S. Pat. Nos. 5,571, 311, 5,609,671, 5,968,243, 5,928,419, 6,323,257, 5,554,739, 5,672,198, 5,698,016, 5,718,746, 5,749,950, 5,803,959, 5,837,045, 5,846,307, 5,895,522, 5,922,118, 6,123,759, 6,221,142, 6,221,143, 6,281,267, 6,329,446, 6,332,919, 6,375,317, 6,287,374, 6,398,858, 6,402,825, 6,468,342, 6,503,311, 6,506,245, and 6,852,156. The disclosures of the preceding references are incorporated by herein by reference.

In one embodiment, the peptide-based dispersants and/or binders of the invention are used in conjunction with a conventional dispersed pigment. In this embodiment, the affinity peptide of the peptide-based dispersant and/or binder has a binding affinity for the pigment or substrate. Therefore, in this embodiment, the coloring composition comprises a dispersed pigment, a carrier medium, and a peptide having the general formula:

wherein: nA⁺ is a positively charged amino acid at the N-terminal end of the peptide; cA⁺ is a positively charged amino acid at the C-terminal end of the peptide; the positively charged amino acid is lysine or arginine, Sn and Sc are optional spacers comprised of 0 to about 20 amino acids; AP is an affinity peptide having an amino acid sequence that has a binding affinity for the pigment or a substrate; x=0 to about 50; y=0 to about 50, provided that x and y may not both be 0. Exemplary peptide sequences for the peptide-based dispersant and/or binder are given by SEQ ID NOs:1, 2, 7, 8, 9, 10, 11, 12, 13, 14, 15, 16, 17, 18, 19, 20, and 21.

In another embodiment, wherein the affinity peptide has a binding affinity for the pigment used in the composition, and therefore functions as a pigment dispersant and a binder, the use of an additional pigment dispersant or a self-dispersed pigment is optional. In this embodiment, the coloring composition comprises a pigment, a carrier medium, and a peptide having the general formula:

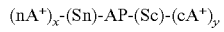

wherein: nA⁺ is a positively charged amino acid at the N-terminal end of the peptide; cA⁺ is a positively charged amino acid at the C-terminal end of the peptide; the positively charged amino acid is lysine or arginine, Sn and Sc are optional spacers comprised of 0 to about 20 amino acids; AP is an affinity peptide having an amino acid sequence that has a binding affinity for the pigment; x=0 to about 50; y=0 to about 50, provided that x and y may not both be 0. Examples of peptide-based dispersants and binders that may be used without an additional dispersant include, but are not limited to those given by SEQ ID NOs:1, 2, 8, 9, 10, 13, 15, 16, and 17.

The coloring compositions of the invention may optionally comprise a film-forming resin or binder. Suitable film-forming resins or binders are water dispersible or water-soluble ionic or nonionic resins. The resins may be acrylic, vinyl, polyurethane, polyester, alkyd, epoxy, or other polymers known to be useful in films. Examples of water-dispersible polymers used in aqueous coloring compositions are described by Savino et al. in U.S. Pat. No. 4,794,147, Salatin et al. U.S. Pat. No. 4,791,168, and Kuwajima et al. U.S. Pat. No. 45,518,724, all of which are incorporated herein by reference.

The coloring composition may further comprise other ingredients that are well known in the art, including, but not limited to crosslinkers, plasticizers, additional cosolvents to aid in stabilization or application of the composition, rheology control agents, UV light stabilizers, antioxidants, catalysts, fungicides, and the like.

The coloring composition may also be a pigment concentrate, so-called because it is generally designed to be diluted as part of a formulation process to make a final product such as an inkjet ink. The pigment content is relatively high, to account for dilution, and the carrier medium is kept simple. The carrier medium for a concentrate can be, for example, simply water, or water with small amounts of soluble organic co-solvent(s) for freezing point depression to aid storage and shipping. The amount of pigment in a concentrate is generally 5-50% by weight and more typically 10-30% by weight of the total weight of concentrate.

In one embodiment the coloring composition is an aqueous ink, such as an inkjet ink. Aqueous ink formulations are well known in the art. For example suitable aqueous ink formulations are described by Ma et al. in U.S. Pat. No. 5,272,201 and by Ma et al. in U.S. Pat. No. 5,085,698, both of which are incorporated herein by reference. Aqueous coloring formulations typically comprise an aqueous carrier medium, a dispersed pigment or a mixture of dispersed pigments, and various other ingredients.

The aqueous carrier medium used in ink formulations comprises water or a mixture of water and at least one water-soluble organic solvent/humectant. Deionized water is commonly used. Representative examples of water-soluble organic solvents/humectants are disclosed in U.S. Pat. No. 5,085,698, supra. The selection of a suitable mixture of water and water-soluble organic solvent depends upon the requirements of the specific application, such as the desired surface tension and viscosity, the selected pigment, drying time of the composition, and the type of substrate onto which the composition will be applied. A mixture of a water-soluble polyhydric alcohol having at least 2 hydroxyl groups, e.g., diethylene glycol, and deionized water is preferred as the aqueous carrier medium, with water comprising between about 30% and about 95%, preferably about 60% to about 95%, by weight, based on the total weight of the aqueous carrier medium. The amount of aqueous carrier medium is in the range of about 70% to about 99.8%, preferably about 94% to about 99.8%, based on total weight of the composition when an organic pigment is selected, and about 25% to about 99.8%, preferably about 70 to about 99.8% when an inorganic pigment is selected.

The dispersed pigment may comprise a single pigment or a mixture of pigments. Examples of suitable pigments are given above. The ink may contain up to about 30% pigment by weight, preferably the amount of pigment is between about 0.1% to about 15% by weight relative to the total weight of the composition. The pigment may be dispersed in the carrier medium using a dispersant or a self-dispersing pigment may be used, as described above. If a dispersant is used in the ink, the dispersant may be present in an amount of about 0.1 to about 10% based on the total weight of the ink.

In one embodiment, the peptide-based dispersants and/or binders of the invention are used in conjunction with a conventional dispersed pigment, as described above. In this embodiment, the ink comprises a dispersed pigment, a carrier medium, and peptide-based dispersant and/or binder. The peptide-based dispersant and/or binder may be present in an amount of about 0.1% to about 30% by weight of the total composition.

In another embodiment, wherein a pigment dispersant and binder is used, the use of an additional pigment dispersant or a self-dispersed pigment is optional. In this embodiment, the ink comprises a pigment and a peptide-based dispersant and binder. The peptide-based dispersant may be present in an amount of about 0.1% to about 30% by weight of the total composition.

The ink may further comprise various types of aqueous additives, which can be used to modify the properties of the ink composition for particular applications. Surfactant compounds may be used in addition to the peptide-based dispersants and/or binders of the present invention. These may be anionic, cationic, nonionic, or amphoteric surfactants. It is known in the art that certain surfactants may be incompatible with certain ink compositions and may destabilize the pigment dispersion. The choice of a specific surfactant is also highly dependent on the type of substrate to be printed. It is expected that one skilled in the art can select the appropriate surfactant for the specific substrate to be used in the particular ink composition. In aqueous inks, the surfactants may be present in the amount of about 0.01% to about 5% and preferably about 0.2% to about 2%, based on the total weight of the ink. Co-solvents to improve penetration and pluggage inhibition properties of the ink composition may also be added, and in fact are preferred. Such co-solvents are well known in the prior art. Additionally, biocides may be used in the ink compositions to inhibit growth of microorganisms. Sequestering agents such as ethylenediaminetetraacetic acid (EDTA) may also be included to eliminate deleterious effects of heavy metal impurities. Other known additives, such as humectants, viscosity modifiers and other acrylic or non-acrylic polymers may also be added to improve various properties of the ink compositions as desired.

The coloring compositions and inks of the invention may be prepared in the same manner as other coloring compositions, such as described by Ma et al. in U.S. Pat. No. 5,272,201.

Method for Dyeing a Substrate

The invention also provides a method for dyeing a substrate comprising applying one of the coloring compositions described above to a substrate under conditions whereby the substrate is dyed. The conditions used for dyeing will depend on the particular substrate and may be readily determined by one skilled in the art using routine experimentation. Suitable substrates include, but are not limited to, the print media given above. The coloring composition may be applied to the substrate using any means known in the art, including, but not limited to, spraying, brushing, screen printing, gravure roll printing, and ink jet printing. Preferably, the coloring composition is applied using ink jet printing. For example, the coloring composition may be applied to the substrate using a conventional ink jet printer, such as an Epson or Hewlett Packard brand desktop ink jet printer. Either continuous ink jet printers or drop-on-demand printers (i.e., piezoelectric or thermal-type) may be used, along with commercially available printheads designed for either industrial or home office applications. The coloring composition is applied to the substrate using the ink jet printer and the pattern may be controlled electronically using computer programming. The coloring composition is then dried on the substrate to form the desired pattern. Typically, the drying is done at a temperature of about 20° C. to about 200° C.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "DMF" means dimethylformamide, "MALDI mass spectrometry" means matrix assisted laser desorption ionization mass spectrometry, "TFA" means trifluoroacetic acid", "wt %" means percent by weight, "P" means pressure, "$P_o$" means initial pressure, "pbw" means parts by weight.

General Methods:

All reagents were obtained from Aldrich Chemicals (Milwaukee, Wis.), unless otherwise specified. Affinity peptides were obtained from SynPep Corporation (Dublin, Calif.).

Examples 1-7

Preparation of Polylysine Capped Affinity Peptides

The purpose of these Examples was to prepare peptides having lysine residues at the N-terminal end by grafting protected polylysine oligomers onto the N-terminus of affinity peptides that have a binding affinity for pigment or print media surfaces. The resulting polylysine capped peptides were deprotected to give the free amine.

Synthesis of ε-Carbobenzyloxylysine N-Carboxyanhydride:

The N-carboxyanhydride of ε-carbobenzyloxylysine was synthesized from ε-carbobenzyloxylysine by phosgenation in dry tetrahydrofuran (THF). A 1,000 mL round bottom, four-necked flask with a thermocouple well was fitted with a calibrated addition funnel that was topped with a small dry ice cold finger. A second, larger cold finger was also fitted to the flask. A magnetic stirring bar was placed in the flask, which was charged with 500 mL of dry THF and 50 g (71 mmol) of ε-carbobenzyloxylysine (Aldrich, Product No. C8008). The contents of the flask were heated to 50° C. prior to phosgene addition. Liquid phosgene (25.4 mL, 142 mmol) was added in two equal portions to the reaction and the reaction mixture was stirred until a slightly cloudy solution was obtained. The solvent was then vacuum distilled at 40° C. or less to dryness and the product was resuspended in 150 mL of dry THF. The solution was then transferred to a dry box and filtered through activated charcoal (Aldrich; product no. 16,1551) and Celite® Diatomaceous Earth (World Minerals Inc., Santa Barbara, Calif.) in separate steps. Then, hexanes (EM Science, Gibbstown, N.J.) were added to initiate crystallization. The solution was placed in a refrigerator at −20° C. for 24 h. The resulting white crystals (2 crops) were collected by vacuum filtration. The resulting yields were 47.32 g and 4.32 g respectively. The correct structure was confirmed by proton NMR in deuterated DMF.

Preparation of Polylysine Capped Affinity Peptides:

The affinity peptides (obtained from SynPep Corporation, Dublin, Calif.) were dried under vacuum. A dried 40 mL glass vial fitted with a silicone rubber septum and magnetic stirring bar was charged with 15 mL of dry DMF. The dried, affinity peptide, as indicated in Table 1, was added to the vial and the contents were stirred until the peptide was completely dissolved. The vial was then placed into a heated aluminum block with stirring and the contents were allowed to equilibrate to a temperature of 50° C. Then, ε-carbobenzyloxylysine N-carboxyanhydride (CbzLys), prepared as described above, was added as a 1 mmol/mL solution in dry DMF, as shown in Table 1, and the contents were allowed to stir for 4 h. The remaining ε-carbobenzyloxylysine N-carboxyanhydride, also in DMF, was injected, as shown in Table 1, and the reactants were allowed to stir at 50° C. for 72 h. The product was collected by evaporating the solvent, washing with hexanes, and then drying in vacuum. Samples of the product were analyzed using MALDI mass spectrometry to confirm the presence of the desired product. The results of the analysis are given in Table 2.

TABLE 1

Synthesis Parameters for Polylysine Capped Affinity Peptides

| Example | Affinity Peptide Name | SEQ ID NO: | Peptide mmol | Total CbzLys mmol | $1^{st}$ Add CbzLys mmol | $2^{nd}$ Add CbzLys mmol |
|---|---|---|---|---|---|---|
| 1 | K/CB71 | 1 | 1.06 | 5.0 | 1.59 | 3.41 |
| 2 | K/SM71 | 2 | 1.10 | 5.0 | 1.66 | 3.34 |
| 3 | CB121 | 3 | 0.39 | 15.0 | 0.58 | 14.42 |
| 4 | CEL121 | 4 | 0.38 | 15.0 | 0.57 | 14.43 |
| 5 | COT71 | 5 | 1.17 | 15.0 | 1.76 | 13.24 |
| 6 | CB72 | 6 | 1.09 | 15.0 | 1.64 | 13.36 |
| 7 | KPPPP/COT72 | 7 | 0.38 | 15.0 | 0.58 | 14.42 |

TABLE 2

Results of Synthesis of Polylysine Capped Affinity Peptides

| Example | Sequence Name | SEQ ID NO: | Yield g | Target Graft Length | Range of Graft Length | Average Graft Length |
|---|---|---|---|---|---|---|
| 1 | K/CB71-polylysine | 8 | 5.661 | 5 | 4-12 | 8 |
| 2 | K/SM71-polylysine | 9 | 2.253 | 5 | 1-10 | 5 |
| 3 | CB121-polylysine | 10 | 4.427 | 15 | 5-20 | 12 |
| 4 | CEL121-polylysine | 11 | 3.181 | 15 | 4-30 | 15 |
| 5 | COT71-polylysine | 12 | 3.67 | 15 | 1-20 | 7 |
| 6 | CB72-polylysine | 13 | 4.185 | 15 | 3-25 | 10 |
| 7 | KPPPP/COT72-polylysine | 14 | 3.423 | 15 | 8-35 | 17 |

The MALDI mass spectrometry results demonstrated that the polylysine capped affinity peptides were formed. The average length of the polylysine graft was dependent on the ratio of N-carboxyanhydride monomer to peptide. The average length of the polylysine graft obtained was less than the targeted chain length in many cases. Presumably this was due to incomplete attachment of the N-carboxyanhydride and to chain transfer processes that resulted in polylysine homopolymer formation.

The grafted polylysine oligomers were deprotected using HBr/acetic acid to remove the carbobenzyloxy groups from the polylysine capped peptides. After deprotection, the lysine residues were converted to the free amine form by the addition of triethylamine. The following procedure was used with the reagent amounts given in Table 3. The polylysine capped affinity peptide was dissolved in trifluoroacetic acid (TFA) contained in a dry glass vial. The HBr/acetic acid reagent was prepared by adding 67.11 mL of a hydrobromic acid solution containing 1.49 g of hydrobromic acid/100 g of solution to 283.33 mL of acetic anhydride solution containing 1.08 g of acetic anhydride/306 g of solution. (Caution: this addition should be made slowly with cooling because substantial heat is generated.) Then, the resulting HBr/acetic acid reagent was added to the vial containing the polylysine capped peptide reagent (10 mL per gram of peptide) and the solution was stirred vigorously for 2 h at room temperature. Diethyl ether (200 to 300 mL) was then added to the reaction mixture. The product was collected by filtration using a 2 μm polytetrafluoroethylene filter (Millipore Corporation, Billerica, Mass.). The collected product was washed with diethyl ether and dried under nitrogen. The product was suspended in a solution of 10% triethylamine in deionized water (20 mL per g of peptide). This solution was placed in dialysis tubing having a molecular weight cut off of 500 Daltons and was dialyzed against deionized water overnight. The solution was removed from the dialysis tubing and was filtered through a 3.1 μm syringe filter. The filtrate was placed in a rotary evaporator, rinsed with approximately 10 mL of deionized water, and then evaporated to dryness. The resulting dried product was dried under vacuum. The product was collected, weighed (see Table 3) and analyzed using MALDI mass spectrometry. The analysis confirmed the removal of the carbobenzyloxy protecting groups.

TABLE 3

Conditions for Deprotecting the Polylysine Capped Affinity Peptides

| Example | SEQ ID NO: | Amount of Peptide g | TFA mL | HBr/acetic acid mL | 10% Triethylamine mL | Recovered weight g |
|---|---|---|---|---|---|---|
| 1 | 8 | 1.0 | 10 | 10 | 10 | 0.12 |
| 2 | 9 | 1.0 | 10 | 10 | 10 | 0.175 |
| 3 | 10 | 2.5 | 25 | 25 | 25 | 0.719 |
| 4 | 11 | 2.5 | 25 | 25 | 25 | 0.878 |
| 5 | 12 | 2.5 | 25 | 25 | 25 | 0.613 |
| 6 | 13 | 2.5 | 25 | 25 | 25 | 0.424 |
| 7 | 14 | 2.5 | 25 | 25 | 25 | 0.564 |

Examples 8-22

Fabric Durability Testing

The purpose of these Examples was to fabricate and test ink compositions comprising polylysine capped affinity peptides. The durability of the resulting compositions when applied to a cotton fabric was tested using an accelerated laundering method.

Ink Formulation:

The polylysine capped affinity peptides, prepared as described in Examples 1-7, were formulated into inks at a level of 2 to 4 wt % using a black ink base, as shown in Table 4. In addition, peptides having lysine or arginine residues at the C-terminus or N-terminus, and control peptides without a terminal positively charged amino acid were obtained from SynPep Corporation. These peptides were also formulated into inks using the black ink base.

A black dispersion was prepared by first mixing well the following ingredients: (i) 210.4 parts by weight (pbw) deionized water, (ii) 80.3 pbw of a 41.5 wt % (solids) anionic polymeric dispersant, and (iii) 9.24 pbw of dimethylethanolamine. The anionic polymer dispersant was a graft co-polymer 66.3/-g-4.2/29.5 POEA(phenoxyethyl acrylate)/-g-ETEGMA(ethoxytriethyleneglycolmethacrylate)/MAA (methyl acrylic acid) prepared according to "Preparation of Dispersant 1" in U.S. Patent Application Publication No. 20030128246 (paragraphs 0122 through 0125), which is incorporated herein by reference, with the ratios of monomers adjusted to obtain the 66.3/4.2/29.5 percent by weight ratios instead of the 61.6/5.8/32.6 percent by weight ratios indicated in the publication. To this was gradually added 100 pbw black pigment (Nipex 180IQ, Degussa). After the pigment was incorporated, 100 pbw deionized water was mixed in to form the millbase, which was circulated through a media mill for grinding. Deionized water (55.4 pbw) was then added for dilution to final strength. This black dispersion (276 g) was mixed with 200 g of glycerol, 120 g of ethylene glycol, 1.6 g of Proxel (Arch Chemicals, Inc., Cheshire, Conn.) 143.6 g of deionized water and 2.5 g of Surfynol® 485 (Air Products, Allentown, Pa.) to form the black ink base. The pH of the ink formulations was adjusted to 7.0, as needed, by addition of 10% phosphoric acid or 10% sodium hydroxide solution.

TABLE 4

Ink Formulations

| Example | SEQ ID NO: | Weight Peptide g | Water g | wt % Peptide | Ink Base g | Pigment g |
|---|---|---|---|---|---|---|
| 8 | 8 | 0.34 | 2.04 | 3.3 | 8 | 0.34 |
| 9 | 9 | 0.34 | 2.04 | 3.1 | 8 | 0.34 |
| 10 | 10 | 0.34 | 2.04 | 3.1 | 8 | 0.34 |
| 11 | 11 | 0.34 | 2.04 | 3.3 | 8 | 0.34 |
| 12 | 12 | 0.34 | 2.04 | 3.3 | 8 | 0.34 |
| 13 | 13 | 0.202 | 1.212 | 2.1 | 8 | 0.34 |
| 14 | 14 | 0.316 | 1.896 | 3.1 | 8 | 0.34 |
| 15 | 1 | 0.5 | 3.0 | 4.2 | 8 | 0.34 |
| 16 | 2 | 0.5 | 3.0 | 4.2 | 8 | 0.34 |
| 17 | 7 | 0.5 | 3.0 | 4.2 | 8 | 0.34 |
| 18 | 15 | 0.34 | 2.04 | 3.2 | 8 | 0.34 |
| 19 | 16 | 0.34 | 2.04 | 3.2 | 8 | 0.34 |
| 20 Comparative | None | 0 | 2.04 | 0 | 8 | 0.34 |
| 21 Comparative | 5 | 0.5 | 3.0 | 4.1 | 8 | 0.34 |
| 22 Comparative | 4 | 0.5 | 3.0 | 4.1 | 8 | 0.34 |

Accelerated Laundering:

The inks were applied to 100% cotton fabric (Cotton Broadcloth Style 419W obtained from Testfabics, West Pittston, Pa.) using drawdown techniques. This process consisted of applying the test ink to a fabric surface using a metal roller to obtain a relatively uniform coating. After application of the ink, the fabric samples were air-dried and then conditioned by heating at 160° C. for 2 min, followed by a cold water prewash prior to the accelerated laundering testing.

The accelerated laundering was done according to American Association of Textile Chemists and Colorists (AATCC) Method 61-1996. Briefly, the dyed cotton samples were loaded into stainless steel canisters with 50 stainless steel balls. The samples were laundered for 45 min at 120° F. (49° C.) with 0.15% detergent. Multifiber swatches were placed in contact with the sample spot during laundering. Color intensity measurements before and after accelerated laundering were determined spectrophotometrically by placing the colored spot region of the fabric into the photosensor and calculating L*, a* and b* parameters representing the photometer response. An initial baseline L* value was measured for the unspotted fabric and all measurements were the average of three individual determinations. Delta E values were calculated from the equation 1 below:

$$\text{Delta } E = ((L^*_1 - L^*_2)^2 + (a_1 - a_2)^2 + (b_1 - b_2)^2)^{1/2} \quad (1)$$

where L*=the lightness variable and a* and b* are the chromaticity coordinates of CIELAB colorspace as defined by the International Commission of Illumination (CIE) (Minolta, *Precise Color Communication—Color Control From Feeling to Instrumentation*, Minolta Camera Co., 1996). The Delta E value correlates with color loss; therefore, smaller values are indicative of better washfastness durability. The results are summarized in Table 5.

TABLE 5

Results of Accelerated Laundering Testing

| Example | Sequence Name | SEQ ID NO: | Delta E |
|---|---|---|---|
| 8 | K/CB71-polylysine | 8 | 0.830 |
| 9 | K/SM71-polylysine | 9 | 1.458 |
| 10 | CB121-polysine | 10 | 3.829 |
| 11 | CEL121-polylysine | 11 | 3.052 |
| 12 | COT71-polylysine | 12 | 5.079 |
| 13 | CB72-polylysine | 13 | 11.223 |
| 14 | KPPPP/COT72-polylysine | 14 | 4.098 |
| 15 | K/CB71 | 1 | 4.811 |
| 16 | K/SM-71 | 2 | 6.823 |
| 17 | KPPPP/COT72 | 7 | 4.643 |
| 18 | CB72/PPPKKKK | 15 | 4.841 |
| 19 | CB72/PPPRRRR | 16 | 6.150 |
| 20 Comparative | No binder | — | 9.925 |
| 21 Comparative | COT71 | 5 | 8.784 |
| 22 Comparative | CEL121 | 4 | 6.233 |

The results demonstrate that the affinity peptides having a positively charged amino acid at the C-terminal and/or N-terminal end have significantly improved washfastness compared to the black ink base (Comparative Example 20) and the affinity peptides without a terminal positively charged amino acid (Comparative Examples 21 and 22). Additionally, affinity peptides having multiple positively charged amino acids at either end of the sequence have superior washfastness compared to the same peptide having a single positively charged amino acid at one end, as can be seen by comparing Examples 8 and 15, 9 and 16, and 14 and 17.

Examples 23-31

Measurement of Peptide-Substrate Binding Energy Using Flow Microcalorimetry

The purpose of these Examples was to measure the strength of the interaction (specifically, the molar heat of adsorption) of affinity peptides, having positively charged terminal amino acid residues, with a cotton substrate using flow microcalorimetry.

Heats of adsorption and desorption for the interaction of the peptides with a cotton substrate were measured with a Model 4034 flow microcalorimeter (Microscal, London, Ltd.). The flow microcalorimeter consisted of a constant temperature metal block which has an inlet and outlet connector which come together inside the unit to form a sample cavity or cell with a volume of 0.17 cm³. A set of two thermistors was embedded in the metal block along with a second set of two thermistors in the sample cavity. The heat changes in the microcalorie range were measured by means of a Wheatstone bridge circuit. The outlet tube was fitted with a 25 μm filter, on which the sample bed sat, and also included a calibration coil. The analog data stream from the Wheatstone circuit was sampled at one-second intervals, digitized and sent to an attached computer for storage and subsequent analysis. All experiments were run at 24.5±0.5° C.

A Waters Model 2410 differential refractometer (Waters Corp., Milford, Mass.) was located downstream of the flow microcalorimeter to monitor mass transfer into and out of the carrier solution. Since no detectable mass transfer was observed for the second adsorption/desorption cycle, this second cycle was used as the blank for the downstream detector. Integrating the time indexed difference between the blank and sample run through the downstream detector produced a concentration peak. Calibration of the peak area was accomplished by injecting the peptide-containing solution into a sample loop of known volume on the downstream detector.

The cotton substrate (cellulose, Sigma Chemical Co., St Louis, Mo., Product No. C6288) was deposited in fiber or particulate form in the sample cell of the instrument. Water was used as the carrier solvent. The carrier solvent was pumped through the sample cell until equilibrium was attained, as evidenced by no change in heat flow into or out of the sample cell. After equilibrium was attained, the solvent stream was switched to one that contained a known concentration of the specific peptide. The adsorption of the peptide onto the substrate resulted in an exothermic peak and a decrease of the peptide concentration in the carrier solvent, as determined downstream using the differential refractive index monitor. The flow of the peptide-containing solvent was continued until equilibrium was attained. Then the solvent stream was switched back to the pure solvent and the desorption of the peptide from the substrate, if any, was monitored. For comparison, a traditional acrylic binder (polymethacrylic acid, 10-mer) was tested for its binding to the substrate using the same method.

The surface area of the cotton substrate used in these studies was measured in order to calculate the mass transfer of the affinity peptides per unit surface area of the substrate surface using the data collected by the refractive index monitor. The surface area determinations were done using dinitrogen adsorption measurements at 77.3° K using a Micromeritics ASAP® Model 2400/2405 porosimeter (Micromeritics Inc., Norcross, Ga.). Samples were degassed overnight at 60° C. prior to data collection. The surface area measurements were made using a five-point adsorption isotherm collected over the relative pressures ($P/P_0$) of 0.05 to 0.20 and were analyzed via the BET method, as described by Brunauer et al. (*J. Am. Chem. Soc.* 60:309 (1938)). The mass transfer value in μmol/m² was calculated by dividing the amount of the sample adsorbed onto the substrate, as determined from the measurements made with the refractive index monitor, by the surface area of the substrate. No significant change in concentration for any of the samples was observed during the desorption step. This result is consistent with irreversible adsorption.

The heats of adsorption from the microcalorimetry determinations were obtained in units of millijoules per square meter (mJ/m²). These values were converted to the molar heats of adsorption, given in units of kilocalories per mole (kcal/mol) in Table 6, by dividing the heat of adsorption by the mass transfer value and using the appropriate conversion factors to obtain the desired units. The negative values for the molar heats of adsorption in the table indicate that the process was exothermic, i.e., heat was given off as a result of the binding.

TABLE 6

Heats of Adsorption for Peptide-Substrate Interaction

| Example | Affinity Peptide Name | SEQ ID NO: | Molar Heat of Adsorption (kcal/mol) |
|---|---|---|---|
| 23 | CB72/PPP/KKKK | 17 | −88.5 |
| 24 | K/PPPP/COT71 | 18 | −179.6 |
| 25 | K/PPPP/COT72 | 19 | −82.2 |
| 26 | K/COT71/PPP/COT72 | 20 | −75.4 |
| 27 | K/COT71/PPP/COT71 | 21 | −102.2 |
| 28 Comparative | None, Polymethacrylic Acid, 10 mer | — | −66.5 |
| 29 Comparative | COT71 | 5 | −20.0 |
| 30 Comparative | CEL71 | 22 | −28.8 |
| 31 Comparative | CEL121 | 4 | −44.5 |

As can be seen from the data in the table, all the molar heats of adsorption for the affinity peptides having a positively charged amino acid residue at one of the ends of their sequence are greater than 70 kcal/mol and are greater than the value obtained for the methacrylate control and the affinity peptides without the terminal positively charged amino acid. These results demonstrate that the peptides having a terminal positively charged amino acid exhibit a stronger binding interaction with the cotton substrate than the methacrylate control and the affinity peptides without the terminal positively charged amino acid.

What is claimed is:

1. A coloring composition for coloring a substrate comprising:
   a) a pigment;
   b) a carrier medium; and
   c) a peptide having affinity for a substrate and having the general formula:

(nA+)x-(Sn)-AP-(Sc)-(cA+)y wherein:
   (i) nA+ is a positively charged amino acid at the N-terminal end of the peptide, selected from the group consisting of lysine and arginine;
   (ii) cA+ is a positively charged amino acid at the C-terminal end of the peptide, selected from the group consisting of lysine and arginine;
   (iii) AP is an affinity peptide having an amino acid sequence that has a binding affinity for the pigment;
   (iv) x=0 to about 50;
   (v) y=0 to about 50; and
   Sn and Sc are optional spacers comprised of 0 to about 20 amino acids;
   provided that x and n may not both be 0; and
   wherein the peptide having affinity for the substrate does not bind covalently to either the pigment or the substrate.

2. A coloring composition for coloring a substrate comprising:
   a) a dispersed pigment;
   b) a carrier medium; and
   c) a peptide having affinity for a substrate and having the general formula:

(nA+)x-(Sn)-AP-(Sc)-(cA+)y wherein:
   (i) nA+ is a positively charged amino acid at the N-terminal end of the peptide, selected from the group consisting of lysine and arginine;
   (ii) cA+ is a positively charged amino acid at the C-terminal end of the peptide, selected from the group consisting of lysine and arginine;
   (iii) AP is an affinity peptide having an amino acid sequence that has a binding affinity for the pigment or the substrate;
   (iv) x=0 to about 50;
   (v) y=0 to about 50; and
   (vi) Sn and Sc are optional spacers comprised of 0 to about 20 amino acids;
   provided that x and y may not both be 0.
   wherein the peptide having affinity for the substrate does not bind covalently to either the pigment or the substrate.

3. A coloring composition according to claim 1 or 2 wherein the pigment is selected from the group consisting of (cyan) Pigment Blue 15:3 and Pigment Blue 15:4; (magenta) Pigment Red 122 and Pigment Red 202; (yellow) Pigment Yellow 14, Pigment Yellow 74, Pigment Yellow 95, Pigment Yellow 110, Pigment Yellow 114, Pigment Yellow 128 and Pigment Yellow 155; (red) Pigment Orange 5, Pigment Orange 34, Pigment Orange 43, Pigment Orange 62, Pigment Red 17, Pigment Red 49:2, Pigment Red 112, Pigment Red 149, Pigment Red 177, Pigment Red 178, Pigment Red 188, Pigment Red 255 and Pigment Red 264; (green) Pigment Green 1, Pigment Green 2, Pigment Green 7 and Pigment Green 36; (blue) Pigment Blue 60, Pigment Violet 3, Pigment Violet 19, Pigment Violet 23, Pigment Violet 32, Pigment Violet 36 and Pigment Violet 38; and (black) carbon black.

4. A coloring composition according to claim 3 wherein the pigment is selected from the group consisting of carbon black, Pigment Blue 15:3, Pigment Blue 15:4, Pigment Red 122, Pigment Red 202, Pigment Yellow 14, Pigment Yellow 74, Pigment Yellow 95, Pigment Yellow 110, Pigment Yellow 128 and Pigment Yellow 155.

5. A coloring composition according to claim 1 or 2 wherein the peptide having affinity for the substrate is from about 5 amino acids in length to about 100 amino acids in length.

6. A coloring composition according to claim 5 wherein the peptide having affinity for the substrate is from about 5 amino acids in length to about 30 amino acids in length.

7. A coloring composition according to claim 5 wherein the peptide having affinity for the substrate is from about 5 amino acids in length to about 20 amino acids in length.

8. A coloring composition according to claim 1 wherein the peptide having affinity for the substrate has a sequence selected from the group consisting of SEQ ID NOs:1, 2, 8, 9, 10, 13, 15, 16, and 17.

9. A coloring composition according to claim 2 wherein the peptide has a sequence selected from the group consisting of SEQ ID NOs:1, 2, 7, 8, 9, 10, 11, 12, 13, 14, 15, 16, 17, 18, 19, 20, and 21.

10. A coloring composition according to claim 1 or 2 wherein the AP affinity peptide is from about 4 to about 20 amino acids in length.

11. A coloring composition according to claim 1 wherein the affinity peptide has a sequence selected from the group consisting of SEQ ID NOs:3, 6, 23, 24, and 25.

12. A coloring composition according to claim 2 wherein the affinity peptide has a sequence selected from the group consisting of SEQ ID NOs:3, 4, 5, 6, 22, 23, 24, 25, and 26.

13. A coloring composition according to claim 2 wherein the dispersed pigment is dispersed using a dispersant.

14. A coloring composition according to claim 13 wherein the dispersant is a peptide-based dispersant.

15. A coloring composition according to claim 13 wherein the dispersant is a random or structured organic polymeric dispersant.

16. A coloring composition according to claim 15 wherein the random or structured organic polymeric dispersant is a polymer comprising monomer units selected from the group consisting of acrylate, methacrylate, butyl methacrylate, 2-ethylhexyl methacrylate, benzylmethacrylate, phenoxyethyl acrylate, and ethoxytriethyleneglycol methacrylate.

17. A coloring composition according to claim 2 wherein the dispersed pigment is a self-dispersing pigment.

18. A coloring composition according to claim 2 wherein the pigment is carbon black, the dispersed pigment is dispersed using an organic polymer comprising acrylate or methacrylate monomers, the peptide is from about 8 to about 50 amino acids in length and the positively charged amino acid is lysine.

19. A coloring composition according claim 1 or 2 wherein the carrier medium is an aqueous carrier medium.

20. A coloring composition according claim 1 or 2 wherein the optional spacers are comprised of amino acids selected from the group consisting of proline, glycine, alanine, serine, glutamic acid, aspartic acid, lysine, histidine, arginine, and mixtures thereof.

21. A coloring composition according to claims 1 or 2 wherein the substrate is selected from the group consisting of printing paper, sheets, films, nonwovens, and textile fabrics.

22. A coloring composition according to claim 21 wherein the substrate is selected from the group consisting of polyester, nylon, silk, cotton, cotton blends, rayon, flax, linen, wool, acetate, acrylic, modacrylic, aramid and polyolefin.

23. A method for dyeing a substrate comprising applying the coloring composition of either of claims 1 or 2 to a substrate under conditions whereby the substrate is dyed.

24. A method according claim 23 wherein the substrate is selected from the group consisting of printing paper, sheets, films, nonwovens, and textile fabrics.

25. A method according to claim 24 wherein the substrate is selected from the group consisting of polyester, nylon, silk, cotton, cotton blends, rayon, flax, linen, wool, acetate, acrylic, modacrylic, aramid and polyolefin.

26. A coloring composition according to either of claims 1 or 2 wherein the peptide has a binding energy to the substrate equal to or greater than 70 kcal/mol.

27. A coloring composition according to either of claims 1 or 2 wherein the composition optionally comprises a formulation agent selected from the group consisting of film-forming resins, binders, plasticizers, rheology control agents, UV light stabilizers, antioxidants, catalysts, and fungicides.

* * * * *